(12) United States Patent
Kamen et al.

(10) Patent No.: US 11,380,084 B2
(45) Date of Patent: Jul. 5, 2022

(54) SYSTEM AND METHOD FOR SURGICAL GUIDANCE AND INTRA-OPERATIVE PATHOLOGY THROUGH ENDO-MICROSCOPIC TISSUE DIFFERENTIATION

(71) Applicant: Siemens Aktiengesellschaft, Munich (DE)

(72) Inventors: Ali Kamen, Skillman, NJ (US); Shanhui Sun, Lexington, KY (US); Terrence Chen, Princeton, NJ (US); Tommaso Mansi, Plainsboro, NJ (US); Alexander Michael Gigler, Untermeitingen (DE); Patra Charalampaki, Leverkusen (DE); Maximilian Fleischer, Höhenkirchen (DE); Dorin Comaniciu, Princeton Junction, NJ (US)

(*) Notice: Subject to any disclaimer, the term of this patent is extended or adjusted under 35 U.S.C. 154(b) by 57 days.

(21) Appl. No.: 16/787,377

(22) Filed: Feb. 11, 2020

(65) Prior Publication Data
US 2020/0175307 A1 Jun. 4, 2020

Related U.S. Application Data

(62) Division of application No. 15/568,219, filed as application No. PCT/US2015/030095 on May 11, 2015, now Pat. No. 10,635,924.

(51) Int. Cl.
G06T 7/00 (2017.01)
G06V 10/44 (2022.01)
(Continued)

(52) U.S. Cl.
CPC .......... G06V 10/454 (2022.01); A61B 5/0036 (2018.08); G06K 9/6274 (2013.01);
(Continued)

(58) Field of Classification Search
CPC .. G06K 9/4628; G06K 9/6274; G06K 9/4671; A61B 5/0036; G06T 7/0012; G06T 7/344; G06T 2207/30024
See application file for complete search history.

(56) References Cited

U.S. PATENT DOCUMENTS

2010/0215239 A1* 8/2010 Assaf ............... A61B 5/055 382/131
2014/0046170 A1* 2/2014 Sun ............... A61B 5/055 600/411
(Continued)

FOREIGN PATENT DOCUMENTS

CN 103886581 A 6/2014
CN 104008095 A 8/2014

OTHER PUBLICATIONS

Hogea et al, "Brain-Tumor Interaction Biophysical Models for Medical Image Registration" (2008). Departmental Papers (MEAM). 163. The American Ceramic Society. Reprinted from Siam Journal of Scientific Computing, vol. 30, Issue 6, Dec. 2008, pp. 3050-3072 (Year: 2008).*

(Continued)

Primary Examiner — Ping Y Hsieh

(57) ABSTRACT

Systems and methods for image classification include receiving imaging data of in-vivo or excised tissue of a patient during a surgical procedure. Local image features are extracted from the imaging data. A vocabulary histogram for the imaging data is computed based on the extracted local image features. A classification of the in-vivo or excised tissue of the patient in the imaging data is determined based on the vocabulary histogram using a trained classifier, which is trained based on a set of sample images with confirmed tissue types.

17 Claims, 9 Drawing Sheets

(51) Int. Cl.
  *G06T 7/33* (2017.01)
  *G06K 9/62* (2022.01)
  *A61B 5/00* (2006.01)
  *G06V 10/46* (2022.01)
(52) U.S. Cl.
  CPC ............ *G06T 7/0012* (2013.01); *G06T 7/344* (2017.01); *G06V 10/462* (2022.01); *G06T 2207/30024* (2013.01)

(56) References Cited

U.S. PATENT DOCUMENTS

| | | | | |
|---|---|---|---|---|
| 2014/0133727 | A1* | 5/2014 | Oktay | G06T 7/33 382/131 |
| 2015/0063713 | A1 | 3/2015 | Yang et al. | |
| 2016/0022125 | A1 | 1/2016 | Nicolau et al. | |
| 2016/0253466 | A1 | 9/2016 | Agaian et al. | |
| 2017/0061617 | A1* | 3/2017 | Cochet | G06T 7/187 |
| 2017/0186156 | A1 | 6/2017 | Isoda et al. | |
| 2018/0096191 | A1 | 4/2018 | Wan et al. | |

OTHER PUBLICATIONS

Nister D et al.: "Scalable Recognition with a Vocabulary Tree", Conference on Computer Vision and Pattern Recognition, 2006 IEEE Computer Society, New York, NY, USA Jun. 17-22, 2006, IEEE, Piscataway, NJ, USA,vol. 2, Jun. 17, 2006 (Jun. 17, 2006), pp. 2161-2168, XP010923119.
Cong Yang et al.: "Deep sparse feature selection for computer aided endoscopy diagnosis",Pattern Recognition,vol. 48, No. 3,Sep. 20, 2014 (Sep. 20, 2014), pp. 907-917, XP029097640.
Christian Jaremenko et al.: "Classification of Confocal Laser Endomicroscopic Images of the Oral Cavity to Distinguish Pathological from Healthy Tissue" In: "INFORMATIKAKTUELL.", Jan. 1, 2015 (Jan. 1, 2015), Springer Verlag, London., GB, XP055246593.
Jiang Menglin et al.: "Computer-aided diagnosis of mammographic masses using vocabulary tree-based image retrieval", 2014 IEEE 11th International Symposium on Biomedical Imaging (ISBI), IEEE, Apr. 29, 2014 (Apr. 29, 2014), pp. 1123-1126, XP032779012.
Sebastian Foersch et al.: "Confocal Laser Endomicroscopy for Diagnosis and Histomorphologic Imaging of Brain Tumors In Vivo", PLOS One, vol. 7, No. 7, Jul. 24, 2012 (Jul. 24, 2012), p. e41760, XP055240172.
Olivier Clatz et al.: "Robust Non-Rigid Registration to Capture Brain Shift from Intra-Operative MRI", IEEE Transactions on Medical Imaging. Jan. 1, 2005 (Jan. 1, 2005). pp. 1417-1427. XP055264244.
Du-Yih Tsai et al.: Information Entropy Measure for Evaluation of Image Quality, Journal of Digital Imaging, vol. 21, No. 3 Sep. 2008, pp. 338-347.
Barbara Andre: "Smart atlas for endomicroscopy diagnosis support: a clinical application of content-based image retrieval", Thesis, ParisTech, Oct. 12, 2011 (Oct. 12, 2011), XP055263227, Retrieved from the Internet: URL:https://hal.inria.fr/file/index/docid/640899/filename/Barbara-Andre-Thesis-Manuscript-Final.pdf (retrieved on Apr. 6, 2016.
Cosmina Hogea et al: "Brain-Tumor Interaction Biophysical Models for Medical Image Registration", Siam Journal on Scientific Computing, vol. 30, No. 6, Dec. 1, 2008 (Dec. 1, 2008), pp. 3050-3072, XP055263414.
David Roberts: "Video: Advancements in image-guided neurosurgery", SPIE TV, Mar. 26, 2015 (Mar. 26, 2015), XP055263656, Retrieved from the Internet: URL:https://www.youtube.com/watch?v=eHAvPiVycaU&list=PLnx7UAe04ET2vxTSmfoe07um69bktH83T&index=1&nohtml5=False [retrieved on Apr. 7, 2016] the whole document & SPIETV: "David Roberts: Advancements in image-guided neurosurgery", Mar. 26, 2015 (Mar. 26, 2015), p. 1, XP054976456.
Jianchao Yang et al: "Linear spatial pyramid matching using sparse coding for image classification", 2009 IEEE Conference on Computer Vision and Pattern Recognition: CVPR 2009; Miami [Beach], Florida, USA, Jun. 20-25, 2009, IEEE, Piscataway, NJ, Jun. 20, 2009 (Jun. 20, 2009), pp. 1794-1801, XP031607284,Pattern Recognition,vol. 48, No. 3, Sep. 20, 2014 (Sep. 20, 2014), pp. 1794-1801, XP031607284.
Olivier Clatz et al: "Patient-Specific Biomechanical Model of the Brain: Application to Parkinson's Disease ProcedureIn: Correct System Design", Jan. 1, 2003 (Jan. 1, 2003). Springer International Publishing. Cham 032548. XP055264143.
Ali Kamen et al: "Automatic Tissue Differentiation Based on Confocal Endomicroscopic Images for Intraoperative Guidance in Neurosurgery", Biomed Research International, vol. 2016. Jan. 18, 2016 (Jan. 18, 2016). pp. 1-8. XP055263355.
Karol Miller: "Biomechanics of the Brain, Ch.4 and 6" In: "Biomechanics of the Brain", Jan. 1, 2011 (Jan. 1, 2011), Springer, XP055264164.
"Image Quality Metrics", Course Material MIT—optical-engineering-spring-2002,Jan. 1, 2002 (Jan. 1, 2002), XP055263675, Retrieved from the Internet: URL:http://ocw.mit.edu/courses/mechanicalengineering/2-717j-optical-engineering-spring-2002/lecture-notes/imgq.pdf.
International Search Report, dated Apr. 26, 2016, International Application No. PCT/US2015/030095, International Filing Date: May 11, 2015, 24 pages.
Breuskin, David, et al. "Confocal laser endomicroscopy in neurosurgery: a new technique with much potential." Minimally invasive surgery. vol. 2013 (2013), 5 pages.
Zhang, Ray R., et al. "Fluorescent Cancer-Selective Alkylphosphocholine Analogs for Intraoperative Glioma Detection." Neurosurgery 76:115-124, 2015.

* cited by examiner

400

500

SYSTEM AND METHOD FOR SURGICAL GUIDANCE AND INTRA-OPERATIVE PATHOLOGY THROUGH ENDO-MICROSCOPIC TISSUE DIFFERENTIATION

CROSS REFERENCE TO RELATED APPLICATIONS

This application is a divisional of U.S. patent application Ser. No. 15/568,219 filed on Oct. 20, 2017, which is a U.S. National Phase Application of PCT/US2015/030095 filed on May 11, 2015, the contents of which are incorporated by reference.

BACKGROUND OF THE INVENTION

The present invention relates generally to surgical guidance and tissue differentiation, and more particularly to surgical guidance and intra-operative pathology through endo-microscopic tissue differentiation.

The therapy of choice for most malignant and benign tumors in the human body is the surgical attempt aimed at total resection of the tumor with preservation of normal functional tissue, followed by radio-chemotherapy. An incomplete resection of a tumor with remaining infiltrative growing cells increases the risk of recurrence with adjacent therapies, decreases the quality of life, and elevates the risk of mortality. Diagnosis of tumor and definition of tumor borders intra-operatively is primarily based on the visualization modalities, where for example a surgeon takes a limited number of biopsy specimens which are later examined through histopathology performed as quickly as possible to provide proper feedback during the surgery. Unfortunately, intraoperative fast histopathology is often not sufficiently informative, due to freezing artifacts, mechanical tissue destruction, and tissue architecture alteration during the sample preparation. In addition, sampling errors are another source of inaccuracy. Optimal surgical therapy, which is the combination of maximal near total resection and minimal injury of the normal tissue, is only achieved if the surgeon is able to identify intra-operatively the tissue cellular structures and differentiate tumorous from normal functional tissue.

BRIEF SUMMARY OF THE INVENTION

In accordance with an embodiment, systems and methods for image classification include receiving imaging data of in-vivo or excised tissue of a patient during a surgical procedure. Local image features are extracted from the imaging data.8 A vocabulary histogram for the imaging data is computed based on the extracted local image features. A classification of the in-vivo or excised tissue of the patient in the imaging data is determined based on the vocabulary histogram using a trained classifier, which is trained based on a set of sample images with confirmed tissue types.

In accordance with on embodiment, systems and methods for image registration include extracting personalized biomechanical parameters from a first region of tissue of a patient in an inverse problem of the biomechanical model using pre-operative imaging data and intra-operative imaging data. Correspondences are identified between an outer layer of a second region of the tissue in the pre-operative imaging data and the outer layer of the second region of the tissue in the intra-operative imaging data. A deformation of an inner layer of the second region of the tissue in the pre-operative imaging data is determined based on the identified correspondences by applying the biomechanical model with the personalized biomechanical parameters.

In accordance with one embodiment, systems and methods for performing tumor resection on a brain of a patient include registering pre-operative imaging data and intra-operative imaging data. The registered pre-operative imaging data and intra-operative imaging data are displayed. A confocal laser endomicroscopy (CLE) probe is navigated to a region of in-vivo or excised brain tissue including the tumor based on the displaying the registered pre-operative imaging data and intra-operative imaging data. CLE imaging data is received from the CLE probe at a border of the tumor. A classification of the region of the in-vivo or excised brain tissue is determined as at least one of healthy tissue and tumorous tissue. The classification of the in-vivo or excised brain tissue is displayed for resection of the tumor. The determining the classification of the region of the in-vivo or excised brain tissue and the displaying the classification of the in-vivo or excised brain tissue are repeated until the displaying the classification of the in-vivo or excised brain tissue shows healthy tissue with a resected tumor bed.

These and other advantages of the invention will be apparent to those of ordinary skill in the art by reference to the following detailed description and the accompanying drawings.

DETAILED DESCRIPTION

The present invention generally relates to surgical guidance and intra-operative pathology through endo-microscopic tissue differentiation. Embodiments of the present invention are described herein to give a visual understanding of methods for surgical guidance and tissue differentiation.

A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Further, it should be understood that while the embodiments discussed herein may be discussed with respect to tumor resection on the brain of a patient, the present principles are not so limited. Embodiments of the present invention may be employed for guidance and classification for any procedure or any subject (e.g., mechanical systems, piping systems, etc.).

Figure 1:
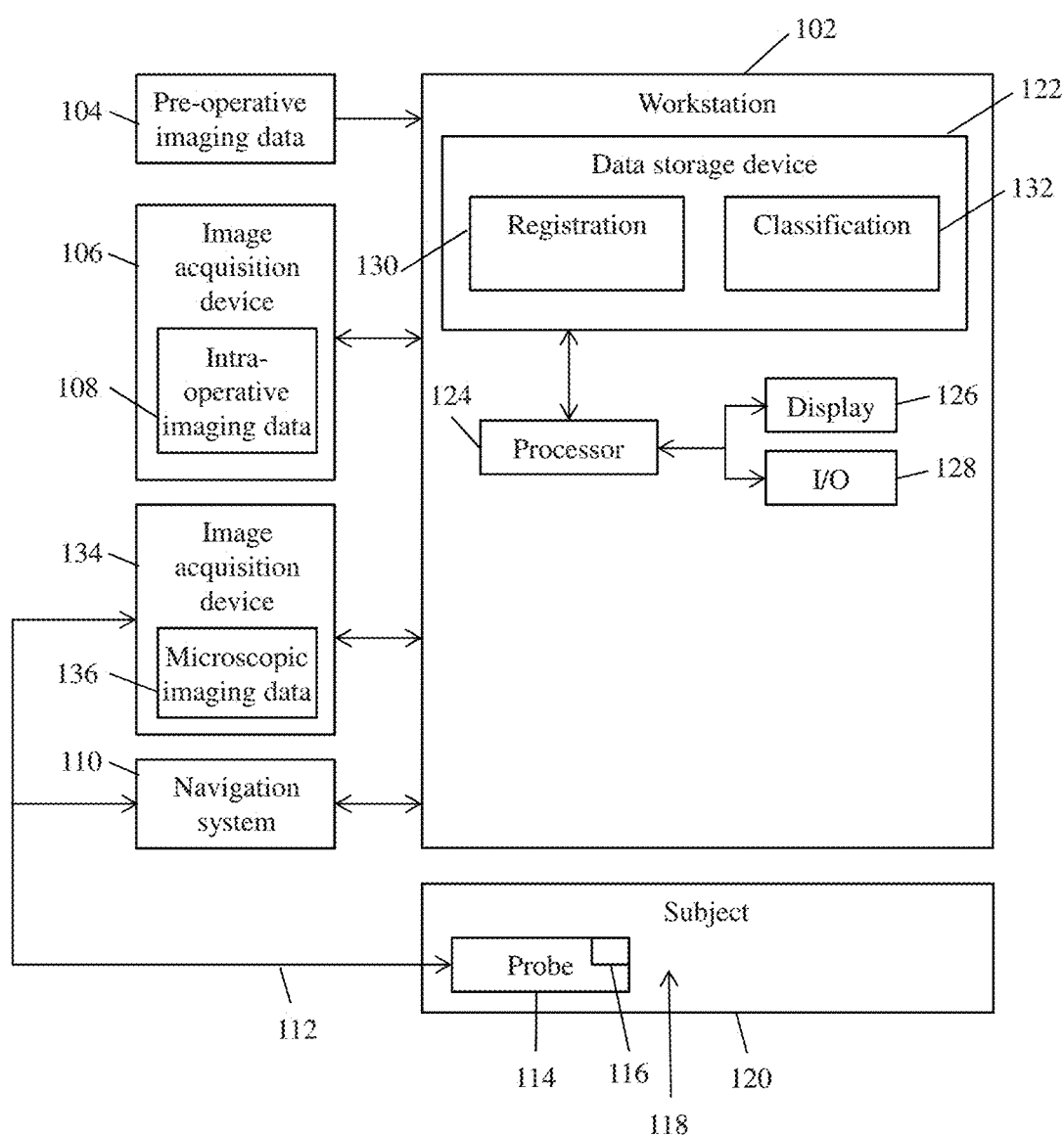
FIG. 1 shows a system for image guidance and classification, in accordance with one embodiment.

FIG. 1 shows a system 100 for image guidance and classification, in accordance with one or more embodiments. System 100 may be employed to provide surgical guidance during a medical (e.g., surgical) procedure (or any other type of procedure), such as a craniotomy. System 100 may be located in a hybrid operating room environment where an image acquisition device is readily available during the course of surgery. Elements of system 100 may be co-located (e.g., within a hybrid operating room environment or facility) or remotely located (e.g., at different areas of a facility or different facilities).

System 100 includes workstation 102 for assisting a user (e.g., a surgeon) during a surgical procedure. Workstation 102 includes one or more processors 124 communicatively coupled to data storage device 122, display device 126, and input/output devices 128. Data storage device 122 stores a plurality of modules representing functionality of workstation 102 when executed on processor 124. It should be understood that workstation 102 may also include additional elements, such as, e.g., a communications interface.

Workstation 102 receives pre-operative imaging data 104 of an area of interest 118 of a subject 120, such as, e.g., a patient. Pre-operative imaging data 104 is acquired prior to a procedure of area of interest 118. Pre-operative imaging data 104 may be of any modality or combination of modalities, such as, e.g., computed tomography (CT), magnetic resonance imaging (MRI), single-photon emission computed tomography (SPECT), positron emission tomography (PET), etc. Pre-operative imaging data 104 includes high resolution imaging data, such as, e.g., images, video, or any other imaging data. Area of interest 118 may include target objects, such as tissue of a patient (e.g., tumorous tissue), as well as other critical structures. The tissue of the patient may be in-vivo tissue or excised tissue (e.g., biopsied tissue). In some embodiments, pre-operative imaging data 104 also includes pre-operative planning information. For example, pre-operative imaging data 104 may be annotated and marked as part of a planning step. In one example, pre-operative imaging data 104 is marked to indicate tumor margin and important anatomical structures to be avoided. Pre-operative imaging data 104 may be received by loading previously stored imaging data of subject 120 from a memory or storage of a computer system.

Workstation 102 also receives intra-operative imaging data 108 from image acquisition device 106 of area of interest 118 of subject 120. Intra-operative imaging data 108 is acquired during an initial phase of the procedure to provide a complete mapping of area of interest 118. Image acquisition device 106 may be of any modality or combination of modalities, such as, e.g., MRI, CT, cone beam CT, etc. Image acquisition device 106 may also employ one or more probes (not shown).

Workstation 102 also receives microscopic imaging data 136 from image acquisition device 134 of area of interest 118 of subject 120. Microscopic imaging data 136 may be received intra-operatively in real-time during a procedure. In some embodiments, image acquisition device 134 may employ one or more probes 114 for imaging area of interest 118 of subject 120. In one embodiment, probe 114 is an endo-microscopic probe, such as, e.g., a confocal laser endomicroscopy (CLE) probe. CLE is an imaging technique which provides microscopic information of tissue in real-time on a cellular and subcellular level.

Probe 114 may be instrumented with tracking device 116 as part of navigation system 110 for tracking the position of the tip of probe 114 within the intra-operative imaging coordinate system. Tracking device 116 may include an optical tracking device, an electromagnetic (EM) tracking device, a mechanical tracking system, or any other suitable tracking device. Probe 114 may also include one or more imaging devices (e.g., cameras, projectors), as well as other surgical equipment or devices, such as, e.g., insufflation devices, incision devices, or any other device. In some embodiments, probe 114 may be tracked and manipulated using microrobots or micro-manipulators in combination with navigation system 110. Image acquisition device 106 is communicatively coupled to probe 114 via connection 112, which may include an electrical connection, an optical connection, a connection for insufflation (e.g., conduit), or any other suitable connection.

In one embodiment, pre-operative imaging data 104 may be acquired of area of interest 118 at an initial (e.g., non-deformed) state while intra-operative imaging data 108 and microscopic imaging data 136 may be acquired of area of interest 118 at a relatively deformed state. For example, pre-operative imaging data 104 may include imaging data of a brain of a patient acquired prior to a craniotomy while intra-operative imaging data 108 and microscopic imaging data 136 may include imaging data of the brain of the patient acquired after the craniotomy (i.e., after the opening of the skull). The opening of the skull may result in a shift or a deformation of brain structures (e.g., the tumor and critical anatomy) due to the change in pressure (relative to before the opening of the skull). Other sources of deformation include the natural movement of subject 120 (e.g., breathing), insufflation, displacement due to instruments or devices, etc. These deformations may be located in the abdominal liver, kidney, or any other location of subject 120.

Registration module 130 is configured to register or fuse pre-operative imaging data 104 and intra-operative imaging data 108 while compensating for the deformation of area of interest 118. Registration module 130 computes deformations and shifts of area of interest 118 using a biomechanical model, which simulates or models movement of an organ (e.g., the brain). In one embodiment, the biomechanical model includes a continuum mechanics model for the brain where the deformation of the entire structure can be inferred from a sparse set of known correspondences within pre-operative imaging data 104 and intra-operative imaging data 108.

Figure 2:
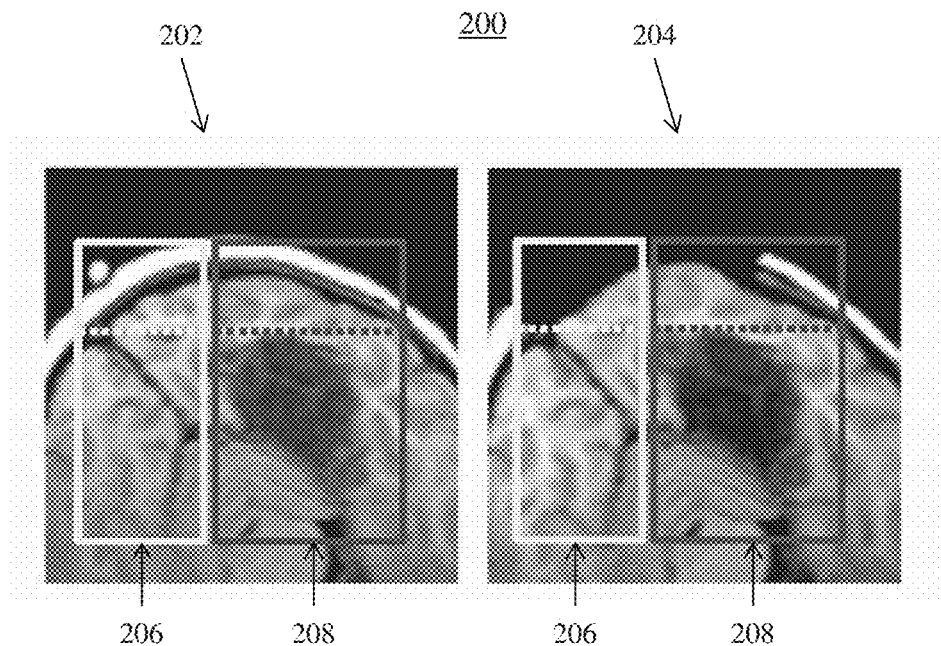
FIG. 2 shows illustrative images of tissue deformation after craniotomy, in accordance with one embodiment.

FIG. 2 illustratively shows images 200 of brain tissue before and after deformation due to a craniotomy, in accordance with one or more embodiments. Image 202 shows a pre-operative image (e.g., of pre-operative imaging data 104) prior to a craniotomy and image 204 shows an intra-operative image (e.g., of intra-operative imaging data 108)

after the craniotomy. Images 200 depict cortical regions (or outer layer regions) in a top portion (shown above the dashed lines) of regions 206 and 208 and subcortical regions (or inner layer regions) in a lower portion (shown below the dashed lines) of regions 206 and 208.

Since the characteristics of image acquisition device 106 acquiring intra-operative image 204 are known a prior, the knowledge of the imaging accuracy of detecting certain subcortical structures is also known. These areas are the primary areas which will be used to estimate the personalized biomechanical parameters. For example, the boundary deformation and inner voxel-based deformations may be used within an inverse problem of the biomechanical model to extract homogeneous and/or non-homogeneous tissue properties. For example, the tissue properties may include tissue elasticity and the Poisson ratio. In another example, pre-operative diffusion tensor MRI may be used to estimate material anisotropy along fibers. Region 206 represents regions where intra-operative imaging data 108 from image acquisition device 106 has higher imaging accuracy of the subcortical regions while region 208 represents regions where image acquisition device 106 has relatively lower imaging accuracy of the subcortical regions.

Personalized (or patient-specific) biomechanical parameters are extracted from region 206 having higher imaging accuracy of the subcortical region. In one embodiment, an inverse problem of the biomechanical model is solved to extract the personalized biomechanical parameters. In an inverse problem, the biomechanical model is applied to deform region 206 of pre-operative image 202 using standard (e.g., nominal or population based) biomechanical parameters. The biomechanical parameters may include, e.g., tissue properties such as the tissue elasticity and Poisson ratio. Other parameters may also be employed. In some embodiments, the biomechanical parameters may be determined based on pre-operative image 202.

The deformed region 206 in pre-operative image 202 is compared with the actual observed deformation in region 206 of intra-operative image 204 using, e.g., a similarity measure. The similarity measure may be performed using known methods. The similarity measure result is used to update the parameters of the biomechanical model. This process may be iteratively repeated (e.g., for a predetermined number of times, until the similarity measure result is maximized or more than a threshold value) to generate personalized biomechanical parameters from region 206.

Once personalized biomechanical parameters are extracted from region 206, correspondences between the cortical layer (i.e., the outer layer of brain) of region 208 of pre-operative image 202 and intra-operative image 204 are identified or established. Pre-operative image 202 is deformed using the biomechanical model based on the correspondences and personalized biomechanical parameters to register pre-operative image 202 and intra-operative image 204. For example, the cortical correspondences may be established between the brain ridges (i.e., interface between the grey matter and cerebrospinal fluid) in both pre-operative and intraoperative images. The intra-operative image 204 could include ultrasound or surface imaging where the topology of brain surface is captured.

Based on the patient specific biomechanical model based registration, a location of a structure (e.g., a tumor) in an inner layer (e.g., subcortical layer) of pre-operative image 202 can be inferred from the intra-operative image 204. The underlying reason is primary due to pre-operative image 202 having much richer information compared to intra-operative image 204.

In one embodiment, to further refine the accuracy of the registration, a model of tumor growth may be employed to estimate the extent of infiltrating cells, which would then locally modify the tissue properties of the biomechanical model. Tumor growth may be modeled using, e.g., a reaction-diffusion scheme, where the reaction term corresponds to the cellular proliferation, and the diffusion term corresponds to the infiltration of the tumor cells. If longitudinal data is available, the parameters of the tumor growth model may be estimated to fit the observed tumor growth. If only one time point is available, the use of PET/SPECT data may be employed to estimate the proliferation rate parameters of the model and infer the extent of the infiltrating cells. In the area of infiltrating cells, the biomechanical models are modified accordingly, and applied for the deformation of pre-operative image 202.

Workstation 102 may display the registered pre-operative imaging data 104 and intra-operative imaging data 108 using display 126 for guidance during a procedure, such as, e.g., tumor resection on the brain. The registered pre-operative imaging data 104 and intra-operative imaging data 108 may be displayed in an, e.g., overlaid configuration, side by side configuration, or any other configuration. In one embodiment, the display of the registered pre-operative imaging data 104 and intra-operative imaging data 108 provides guidance for navigating probe 114 acquiring microscopic imaging data 136. For example, microscopic imaging data 136 may include microscopic information of tissue on a cellular and subcellular level.

Classification module 132 is configured to automatically classify microscopic imaging data 136 for tissue differentiation during the procedure. For example, classification module 132 may classify tissue in microscopic imaging data 136 according to, e.g., healthy tissue or tumorous tissue, a particular type of tumor, a particular grade of tumor, or any other classification.

In one embodiment of classification module 132, a bag of words (e.g., features) approach is employed for image classification. In the bag of words approach, global image features are represented by vectors of occurrence counts of visual words. For example, global image features may be represented in a histogram of a vocabulary dictionary determined based on local image features. These global image features are then used for classification.

Figure 3:
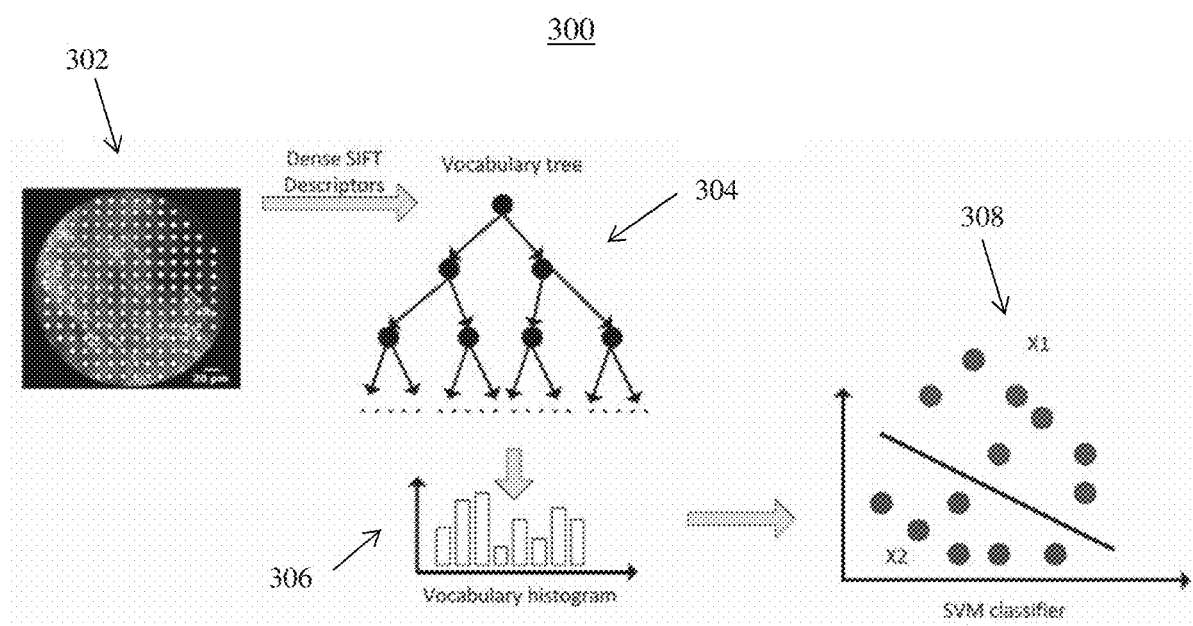
FIG. 3 shows a high-level framework for image classification, in accordance with one embodiment.
Figure 4:
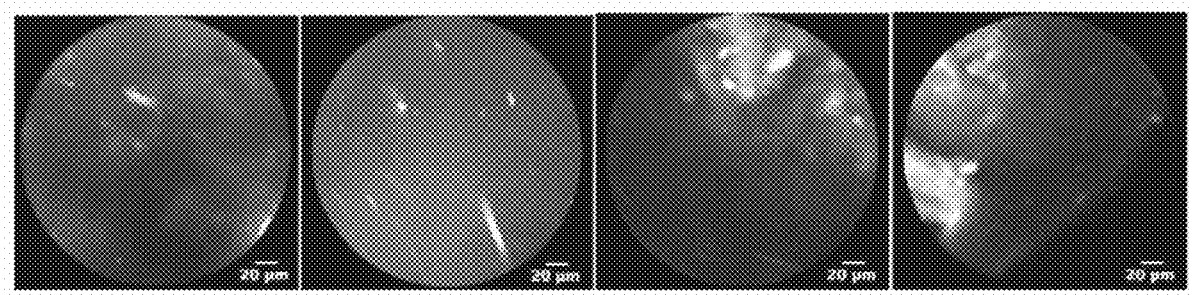
FIG. 4 illustratively shows images having low texture information, in accordance with one embodiment.

FIG. 3 shows a high-level framework 300 for image classification, in accordance with one or more embodiments. At step 302, local image features are extracted from microscopic imaging data 136 (e.g., acquire with CLE probe) to be classified. Images from microscopic imaging data 136 with low image texture information may have less value for image classification. As such, these images can be preliminarily excluded from classification. FIG. 4 illustratively shows images 400 having low texture information, in accordance with one or more embodiments. Images 400 may be excluded from classification.

In one embodiment, images from microscopic imaging data 136 are excluded from classification based on an entropy value E of each image as compared to a predetermined threshold value. Entropy E is shown in equation (1).

$$E = -\Sigma_{i \in (0,255)} p_i \log(p_i) \tag{1}$$

where $p_i$ is the probability of pixel values in a region of interest R of an image. The region of interest R may be the lens area. Probability $p_i$ may be calculated by representing pixel values in the region of interest R as a histogram of image intensities inside the region of interest R.

Local image features are then extracted from the remaining images of microscopic imaging data 136. In one embodiment, scale-invariant feature transform (SIFT) descriptors are extracted from the remaining images as the local image features. SIFT descriptors describe an invariant local image structure and capture local texture information. SIFT descriptors are computed for every $n_s$ pixels inside the region of interest R of each remaining imaging in microscopic imaging data 136, where $n_s$ can be any positive integer. Each image is represented having a width w and height h. Other local image features may also be employed, such as, e.g., local binary pattern (LBP), histogram of oriented gradient (HOG), or any other descriptor or any combination of descriptors.

Figure 5:
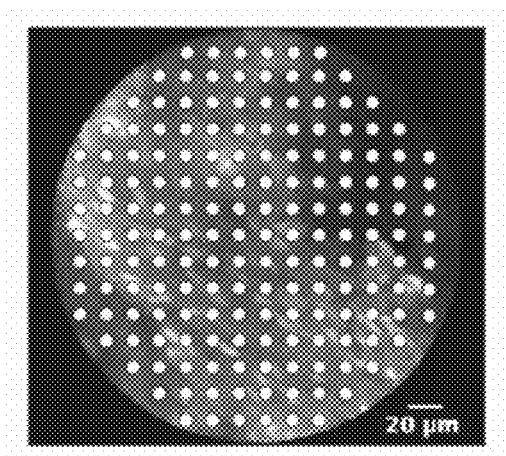
FIG. 5 illustratively shows local image feature sampling inside a region of interest of an intra-operative image, in accordance with one embodiment.

FIG. 5 illustratively shows local image feature sampling inside region of interest R of an image of microscopic imaging data 136, in accordance with one or more embodiments. Each white dot in image 500 represents a location where a SIFT descriptor is computed. In one embodiment, 128 dimension SIFT features are used however other dimensions may also be employed.

At step 304, a vocabulary tree is learned for the extracted local image features. The vocabulary tree may be utilized to construct the vocabulary dictionary. The vocabulary tree defines a hierarchical quantization using, e.g., hierarchical k-means clustering. In one embodiment, a complete binary (i.e., k=2) search tree structure is employed having $2^{n_d}$ leaf nodes, where $n_d$ is the predetermined depth of the binary tree. The leaf nodes are used as the visual vocabulary words.

Figure 6:
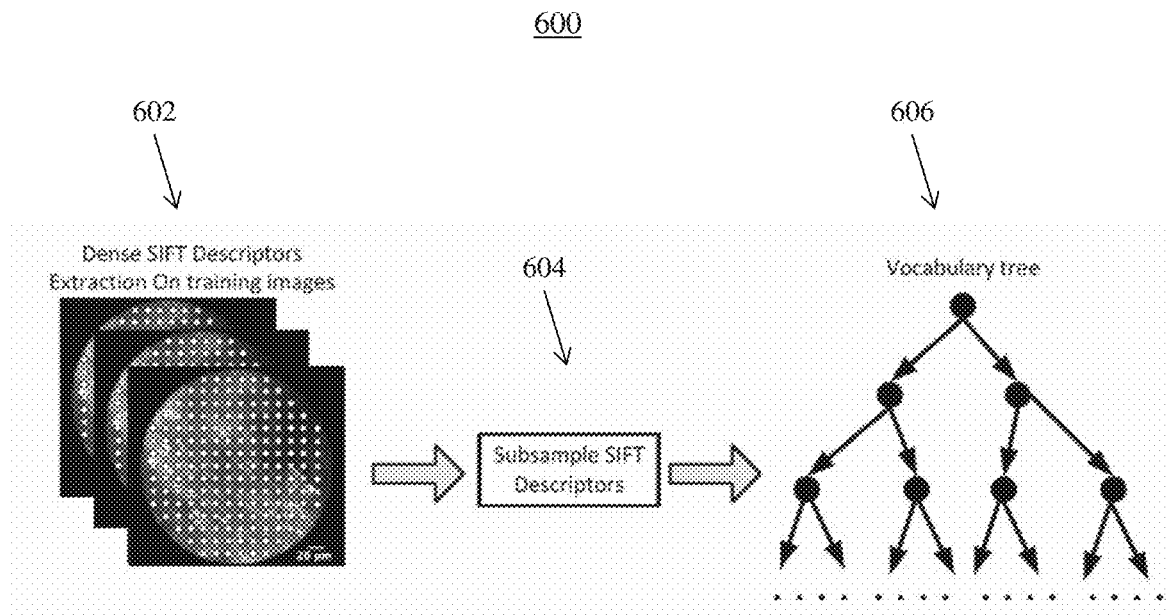
FIG. 6 shows an overview of vocabulary tree training, in accordance with one embodiment.

The vocabulary tree is trained in an offline training stage. FIG. 6 shows an overview 600 of vocabulary tree training, in accordance with one or more embodiments. Vocabulary tree training uses training data 602 representing a collection of training SIFT descriptors (or any other local image features) derived from a training dataset. A subsample 604 of $N_v$ samples are randomly selected from the training SIFT descriptors, where $N_v$ may be any positive integer. A k-means clustering algorithm (k=2) is initially applied to the selected subsample 604 of the training SIFT descriptors. Generally, in an initial step, k centroids or cluster centers (e.g., 2) are defined, one for each cluster. Then, SIFT descriptors of subsample 604 are assigned to a respective cluster having a closest centroid. This process is recursively applied for each resulting cluster until the tree depth reaches $n_d$ to train vocabulary tree 606. Each leaf node in the vocabulary tree may be associated with a label or vocabulary describing each leaf node. The vocabulary tree encodes most prominent discriminate features extracted from images, which will then be used to classify regions of a new image (from a new patient).

In an online stage for classifying an image of microscopic imaging data 136, SIFT descriptors (i.e., feature vectors) extracted from the image are sorted in the trained vocabulary tree. Each feature vector is passed down the trained vocabulary tree 304 level by level by comparing the respective feature vector to the two cluster centers at each level and choosing the closest cluster center to that respective feature vector. Vocabulary histogram 306 is computed for all SIFT descriptors on each image by determining a number of SIFT descriptors for the respective image located at each of the leaf nodes of the trained vocabulary tree 304. Vocabulary histogram 306 is a histogram of the number of local image features from an image sorted to each vocabulary term associated with a leaf node in the vocabulary tree. The vocabulary histogram 306 represents a global image feature for an image. Each image is summarized based on a frequency of appearance of a certain set of features signified as in the feature vocabulary. The histogram of the feature vocabulary is one way to summarize the image contents as it relates to the various important features to identify specific tumor pattern.

A classifier 308 such as, e.g., an SVM classifier is used to classify the image based on the global image feature (e.g., vocabulary histogram 306). Classifier 308 classifies tissue, e.g., as healthy tissue or tumorous tissue, as a particular grade of tumor, as one of multiple different tumor types, or any other classification. Classifier 308 may include any suitable classifier, such as, e.g., a random forest classifier, a K-nearest neighbor classifier, etc. Classifier 308 may be trained in an offline training step based on vocabulary histograms determined for sample images in a training set having confirmed tissue types. In one embodiment, a marginal space deep learning (MSDL) based framework may be employed to perform image classification. In this case, an auto-encoder convolutional neural network (CNN) may be used to train the marginal space learning (MSL) classifier.

In some embodiments, instead of using hands-on local image descriptors, rotationally invariant filter banks may be utilized to generate a local response. In this embodiment, vocabulary tree 304 is trained using filter bank responses.

In another embodiment of classification module 132, instead of using a hierarchical vocabulary tree to quantize local descriptors into global image features, classification module 132 employs a sparse coding method as represented in equation (2).

$$\min_c \Sigma_{i=1}^N \|x_i - B c_i\|^2 + \lambda |c_i| \qquad (2)$$

B is a given code book, which may be obtained using k-means cluster, a vocabulary tree (e.g., as discussed above), or directly learned from data. $x_i$ is a local feature descriptor, such as, e.g., a SIFT descriptor. $c_i$ is the vector of sparse coefficient. Parameter $\lambda$ is used to control sparsity. The goal is to learn $c_i$.

Histogram z is used as a global image feature for classification. Histogram z is shown in equation (3).

$$z = \frac{1}{M} \sum_{i=1}^{M} c_i \qquad (3)$$

where M is the number of local descriptors on each image. Histogram z is used as a global image feature for classification. Histogram z is shown in equation (3).

In one embodiment, instead of average pooling (as in a histogram), a max pooling function is employed as in equation (4).

$$z_j = \max_{i \in \{1, 2, \ldots, M\}} \{|c_{j1}|, |c_{j2}|, \ldots, |c_{ji}|, \ldots, |c_{jM}|,\} \qquad (4)$$

where $z_j$ is the jth element of z, corresponding to jth basis of B. $c_{ji}$ is the jth element of the sparse coefficient. $c_i$ is the ith local descriptor on each image. Histogram z is input into a classifier (e.g., an SVM classifier) to classify the image.

Advantageously, workstation 102 aids a user during a procedure of subject 120. For example, workstation 102 may display the registered intra-operative imaging data 108 and pre-operative imaging data 104 using display 126 in an, e.g., overlaid configuration, a side-by-side configuration, or any other configuration to provide guidance to the user. The display of the registered intra-operative imaging data 108 and pre-operative imaging data 104 may be augmented with the location of probe 114. Display 126 may further display microscopic imaging data 136 with the registered images (e.g., side-by-side, overlaid, etc.). In some embodiments, display 126 displays the registered pre-operative imaging data 104 including the planning information (e.g., annotations and marks).

In some embodiments, workstation 102 may display different types of tissue according to, e.g., tumor type or grade, healthy tissue, etc. For example, workstation 102 may display results of the classification using display 126. In this manner, a surgeon or other user can confirm the results before proceeding to the next step. The results of the classification may be displayed on display 126 having color coded overlays over pre-operative imaging data 104, intra-operative imaging data 108, and/or microscopic imaging data 136. For example, red may be used to indicate tumorous tissue while green may indicate healthy tissue. Other forms of visual identifiers are also contemplated. In some embodiments, microscopic imaging data 136 from prior procedures may be loaded from a memory or storage of a computer system and registered and displayed within a current intra-operative imaging coordinate system. In further embodiments, workstation 102 provides reports of image sequences taken at different anatomical locations as indicated within pre-operative imaging data 104 and/or post-operative images.

Figure 7:
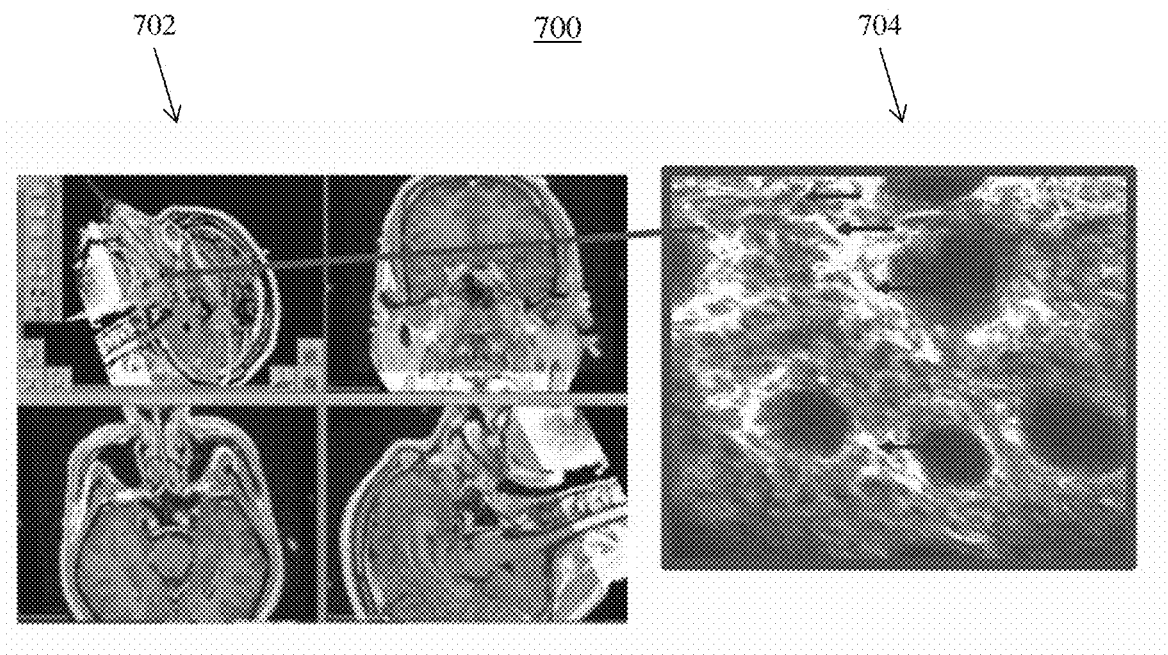
FIG. 7 shows an exemplary display of a workstation, in accordance with one embodiment.

FIG. 7 shows an exemplary display 700 of workstation 102 using display 126, in accordance with one or more embodiments. Display 700 includes view 702 showing the registered pre-operative imaging data 104 and intra-operative imaging data 108 augmented with location of probe 114. Display 700 may also include view 704 of probe 114. In this manner, a user (e.g., a surgeon) not only sees the anatomical structures as depicted by the registered images in view 702, but also can see cellular and subcellular level structures of the tissue at the tip of (e.g., CLE) probe 114 in view 704.

Figure 8:
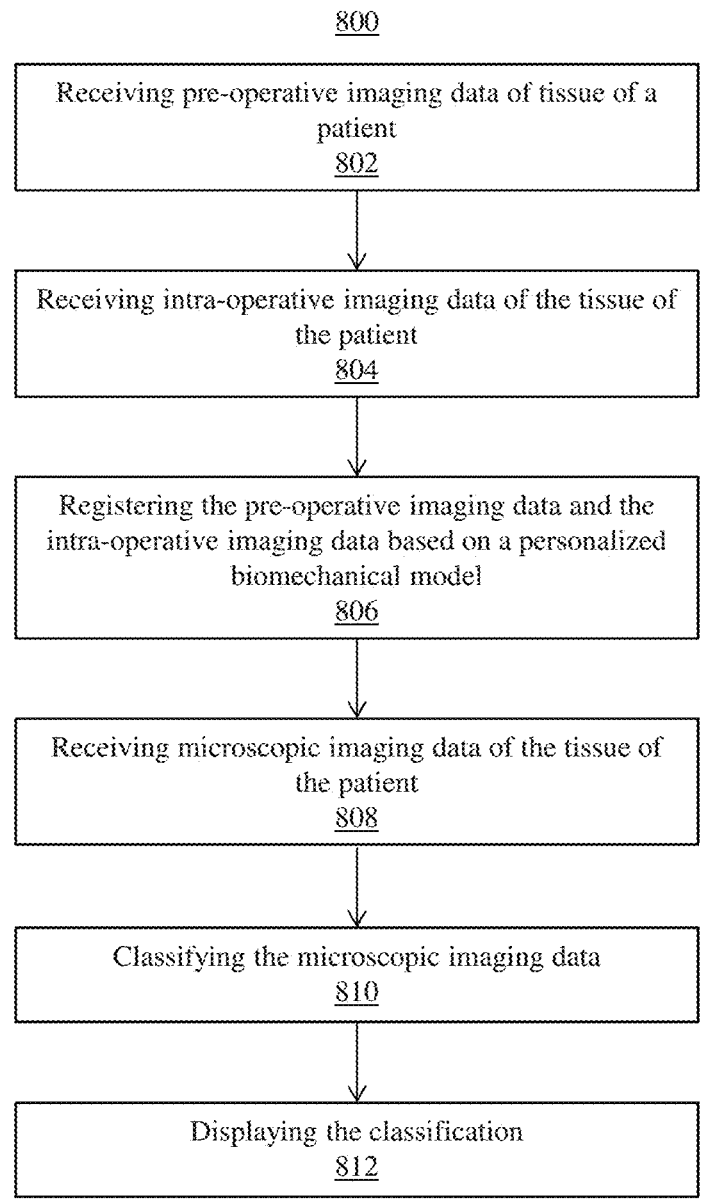
FIG. 8 shows a method for image guidance and classification, in accordance with one embodiment.

FIG. 8 shows a method 800 for image guidance and classification, in accordance with one or more embodiments. At step 802, pre-operative imaging data of tissue of a patient is received. The pre-operative imaging data is acquired prior to a procedure. The pre-operative imaging data may be of any modality, such as, e.g., CT, MRI, SPECT, PET, etc. The pre-operative imaging data may be images of the tissue of the patient at an initial (i.e., non-deformed) state. In one embodiment, the pre-operative imaging data may be received by loading previously stored imaging data of subject 120 from a memory or storage of a computer system.

At step 804, intra-operative imaging data of the tissue of the patient is received. The intra-operative imaging data may be acquired at an initial phase of the procedure. The intra-operative imaging data may be of any modality, such as, e.g., MRI, CT, cone beam CT, etc. The intra-operative imaging data may be of images of the tissue of the patient at a deformed state. For example, the intra-operative imaging data may be of brain tissue of a patient after a craniotomy.

Figure 9:
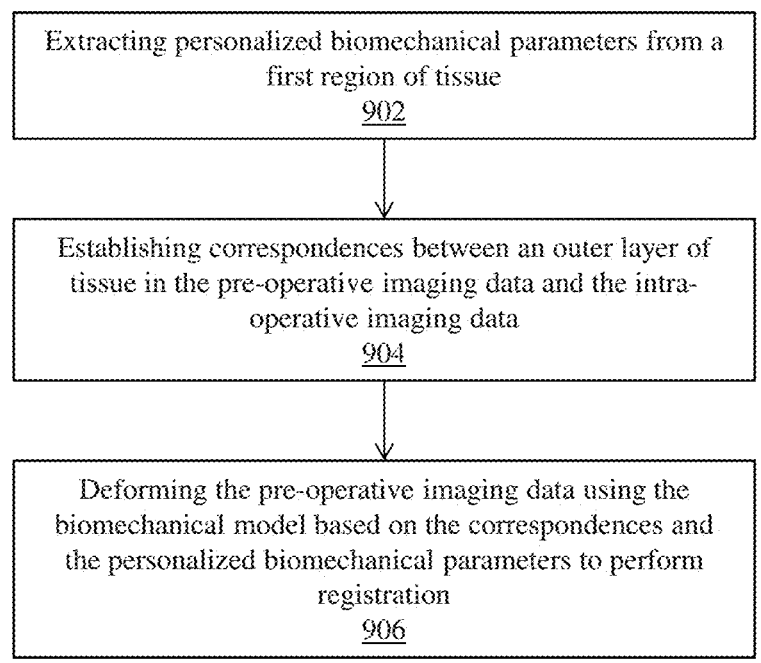
FIG. 9 shows a detailed method for registering pre-operative imaging data and intra-operative imaging data based on a personalized biomechanical model, in accordance with one embodiment.

At step 806, the pre-operative imaging data and the intra-operative imaging data are registered based on a personalized biomechanical model. In one embodiment, the biomechanical model includes a continuum mechanics model for the brain. FIG. 9 shows a method 806 for registering the pre-operative imaging data and the intra-operative imaging data based on the personalized biomechanical model, in accordance with one or more embodiments.

At step 902, personalized biomechanical parameters are extracted from a first region of tissue by solving an inverse problem of the biomechanical model. The first region may have a higher imaging accuracy in an inner layer (e.g., subcortical layer) of the tissue. The biomechanical model is initially applied to deform the first region of tissue in the pre-operative imaging data using standard (e.g., nominal or population based) biomechanical parameters. The biomechanical parameters may include, e.g., elasticity and the Poisson ratio. The deformed first region in the pre-operative imaging data is compared to the first region in intra-operative imaging data using a similarity measure. Similarity measure results are used to update the biomechanical parameters. This process is iteratively repeated to extract personalized biomechanical parameters from the first region.

At step 904, correspondences between an outer layer (e.g., cortical layer) of a second region of tissue are established between the pre-operative imaging data and the intra-operative imaging data. The second region of tissue having have a lower imaging accuracy in the inner layer of tissue.

At step 906, the pre-operative imaging data is deformed using the biomechanical model based on the correspondences and the personalized biomechanical parameters to register the pre-operative imaging data and intra-operative imaging data. In one embodiment, a model of tumor growth may be employed to estimate the extent of infiltrating cells. The biomechanical parameters may be modified in accordance with the model of tumor growth.

Returning to FIG. 8, at step 808, microscopic imaging data of the tissue of the patient is received. The microscopic imaging data may be intra-operatively acquired during a surgical procedure. The microscopic imaging data may be acquired using a CLE probe to provide microscopic information of tissue on a cellular and subcellular level. The CLE probe may be tracked using a tracking device and navigation system within a common coordinate system of the registered images.

Figure 10:
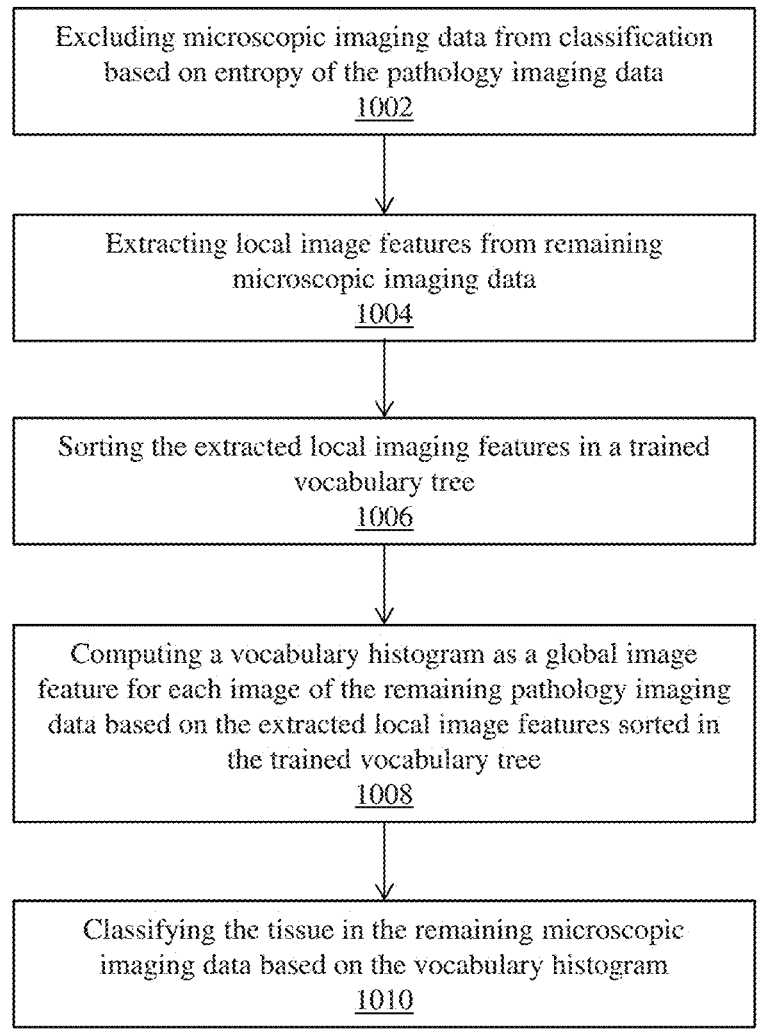
FIG. 10 shows a detailed method for classifying tissue, in accordance with one embodiment.

At step 810, the microscopic imaging data are classified. For example, the microscopic imaging data may be classified as, e.g., healthy or tumorous tissue, a particular grade of tumor, a particular type of tumor. FIG. 10 shows a method 810 for classifying microscopic imaging data, in accordance with one or more embodiments.

At step 1002, images of the microscopic imaging data are excluded from classification based on an entropy of the images. For example, microscopic imaging data having an entropy less than a threshold value may be excluded from classification as having low image texture information.

At step 1004, local image features are extracted from the remaining microscopic imaging data. The local image features may include SIFT descriptors or any other suitable local image features, such as, e.g., LBP, HOG, or any other local image feature or combination of local image features. The local image features may be sampled at every $n_s$ pixels of a region of interest, $n_s$ is any positive integer.

At step 1006, the extracted local image features are sorted in a trained vocabulary tree. The trained vocabulary tree may be a binary vocabulary tree learned using hierarchical k-means cluster (k=2). Each extracted local image feature (i.e., feature vector) is passed down the trained vocabulary tree level by level by comparing the respective feature vector with two cluster centers and choosing a closest cluster center to that respective feature vector. The trained vocabulary tree may be learned in an offline training step using training data.

At step 1008, a vocabulary histogram is computed as a global image feature for each image of the remaining microscopic imaging data based on the extracted local image features sorted in the trained vocabulary tree. A number of SIFT descriptors located in the leaf nodes of the trained vocabulary tree is determined for each respective image of the remaining microscopic imaging data to compute the vocabulary histogram. The vocabulary histogram may be based on an average pooling function or a max pooling function.

At step 1010, the tissue of the patient in the remaining microscopic imaging data is classified based on the vocabulary histogram. The tissue of the patient may be classified as, e.g., healthy or tumorous, a particular grade of tumor, a particular type of tumor, etc. A trained classifier, such as, e.g., SVM, random forest, K-nearest neighbor, or any other suitable classifier may be applied to classify the tissue according to grade of tumor, healthy tissue, etc.

Returning to FIG. 8, at step 812, the classification is displayed. For example, the classification may be displayed as color coded overlays over the registered pre-operative imaging data and/or intra-operative imaging data and/or the microscopic imaging data. The registered pre-operative imaging data and intra-operative imaging data, as well as the microscopic imaging data, may be displayed in a side-by-side configuration, an overlaid configuration, or any other configuration. A location of a probe used to acquire the microscopic imaging data may also be displayed in the registered pre-operative imaging data and intra-operative imaging data.

Figure 11:
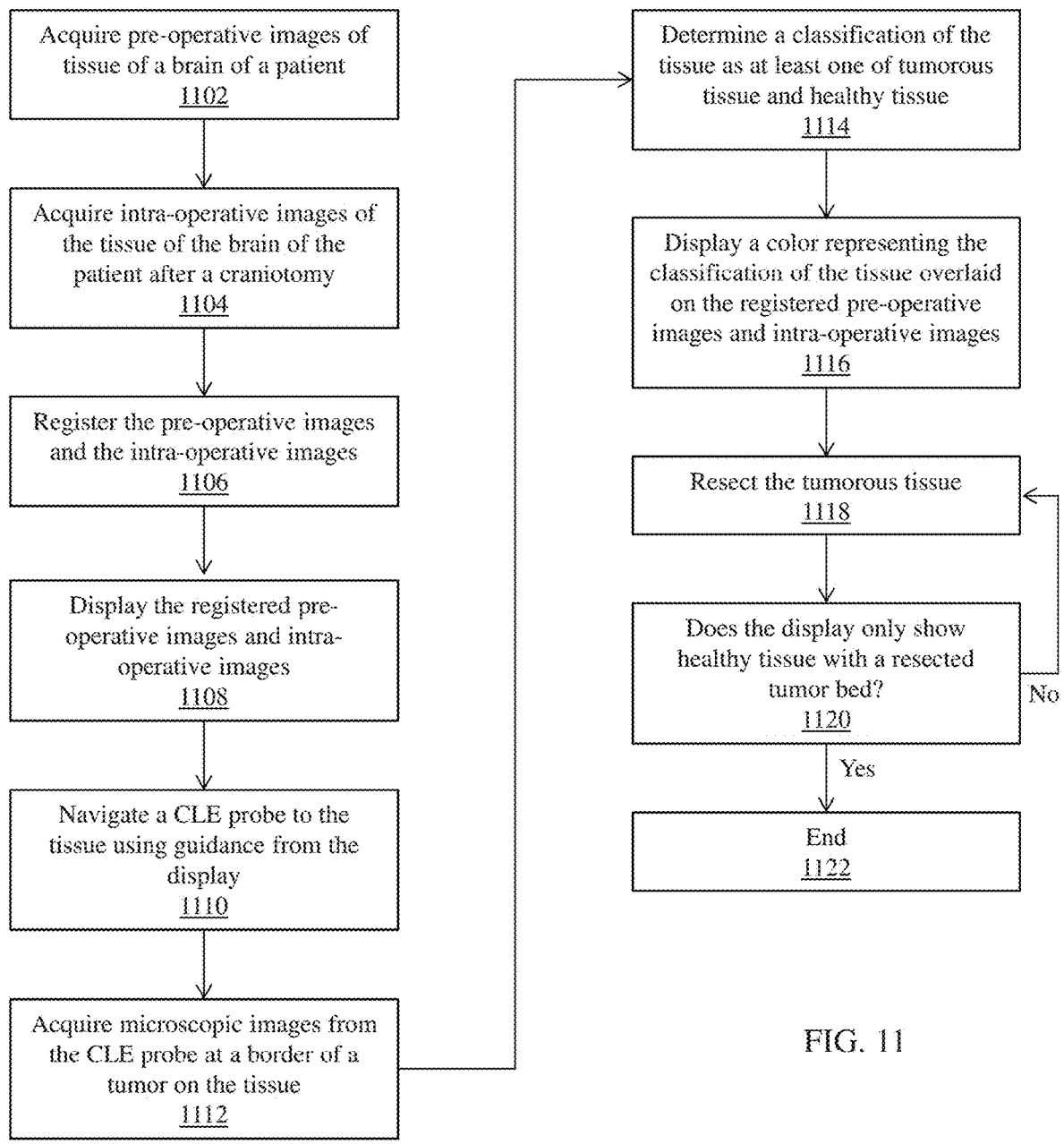
FIG. 11 shows a high-level workflow for a tumor resection procedure of the brain, in accordance with one embodiment.

FIG. 11 shows a high-level workflow 1100 for a tumor resection procedure of the brain, in accordance with one or more embodiments. In step 1102, pre-operative images of tissue of a brain of a patient are acquired. The pre-operative images may be annotated or marked with planning information. The tissue may include a tumor. At step 1104, intra-operative images of the tissue of the brain of the patient are acquired after a craniotomy. The craniotomy causes a deformation in the tissue of the brain due to the change in pressure. At step 1106, the pre-operative images and intra-operative images are registered, e.g., using a biomechanical model with personalized biomechanical parameters. At step 1108, the registered pre-operative images and intra-operative images are displayed using a display device. The registered pre-operative images and intra-operative images may be displayed in a side-by-side configuration, an overlaid configuration, or any other configuration.

At step 1110, a CLE probe is navigated to the tissue using guidance from the display device. The location of the CLE probe may be displayed with the registered pre-operative images and intra-operative images using a tracking device instrumented on the CLE probe. At step 1112, microscopic images are acquired from the CLE probe of at a border of the tumor on the tissue. At step 1114, a classification of the tissue is determined in the microscopic images as at least one of tumorous tissue (or a type/grade of tumorous tissue) and healthy tissue. At step 1116, a color representing the classification of the tissue is displayed as being overlaid on the registered pre-operative images and intra-operative images. For example, a red overlay may indicate tumorous tissue while a green overlay may represent healthy tissue. At step 1118, the tumor is resected. At step 1120, the classification is updated and displayed. If the display only shows healthy tissue, the procedure ends at step 1122. However, if the display shows tumorous tissue, workflow 1100 returns to step 1118 and the tumorous tissue is again resected.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIGS. 8-11. Certain steps of the methods described herein, including one or more of the steps of FIGS. 8-11, may be performed by a server or by another processor in a network-based cloud-computing system. Certain steps of the methods described herein, including one or more of the steps of FIGS. 8-11, may be performed by a client computer in a network-based cloud computing system. The steps of the methods described herein, including one or more of the steps of FIGS. 8-11, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 8-11, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 12:
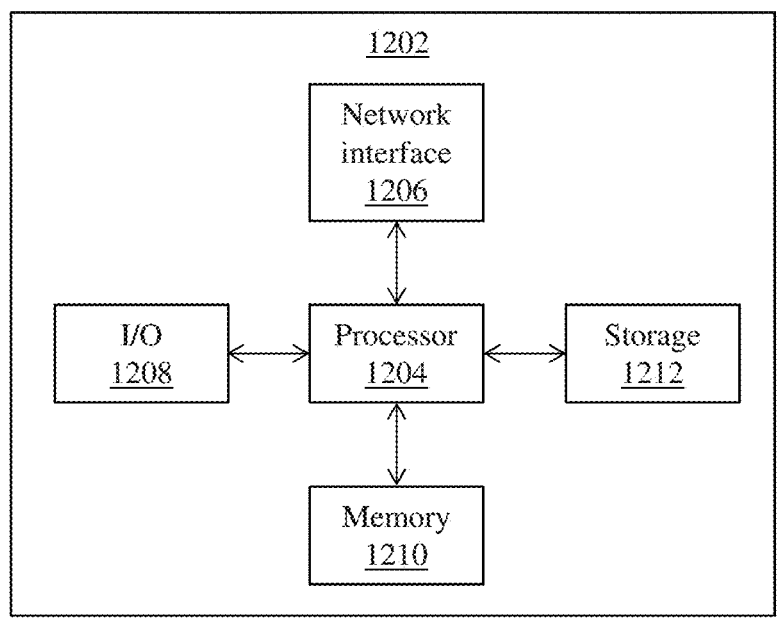
FIG. 12 shows a high-level block diagram of a computer for image guidance and classification, in accordance with one embodiment.

A high-level block diagram 1200 of an example computer that may be used to implement systems, apparatus, and methods described herein is depicted in FIG. 12. Computer 1202 includes a processor 1204 operatively coupled to a data storage device 1212 and a memory 1210. Processor 1204 controls the overall operation of computer 1202 by executing computer program instructions that define such operations. The computer program instructions may be stored in data storage device 1212, or other computer readable medium, and loaded into memory 1210 when execution of the computer program instructions is desired. Thus, the method steps of FIGS. 8-11 can be defined by the computer program instructions stored in memory 1210 and/or data storage device 1212 and controlled by processor 1204 executing the computer program instructions. For example, the computer program instructions can be implemented as computer executable code programmed by one skilled in the art to perform the method steps of FIGS. 8-11 and the modules of FIG. 1. Accordingly, by executing the computer program instructions, the processor 1204 executes the method steps of FIGS. 8-11 and modules of FIG. 1. Computer 1204 may also include one or more network interfaces 1206 for communicating with other devices via a network. Computer 1202 may also include one or more input/output devices 1208 that enable user interaction with computer 1202 (e.g., display, keyboard, mouse, speakers, buttons, etc.).

Processor 1204 may include both general and special purpose microprocessors, and may be the sole processor or one of multiple processors of computer 1202. Processor 1204 may include one or more central processing units (CPUs), for example. Processor 1204, data storage device 1212, and/or memory 1210 may include, be supplemented by, or incorporated in, one or more application-specific integrated circuits (ASICs) and/or one or more field programmable gate arrays (FPGAs).

Data storage device 1212 and memory 1210 each include a tangible non-transitory computer readable storage medium. Data storage device 1212, and memory 1210, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1208 may include peripherals, such as a printer, scanner, display screen, etc. For example, input/output devices 1280 may include a display device such as a cathode ray tube (CRT) or liquid crystal display (LCD) monitor for displaying information to the user, a keyboard, and a pointing device such as a mouse or a trackball by which the user can provide input to computer 1202.

Any or all of the systems and apparatus discussed herein, including elements of workstation 102, image acquisition device 106, and navigation system 110 of FIG. 1, may be implemented using one or more computers such as computer 1202.

One skilled in the art will recognize that an implementation of an actual computer or computer system may have other structures and may contain other components as well, and that FIG. 12 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for image registration, comprising:
   extracting personalized biomechanical parameters from a first region of tissue of a patient in an inverse problem of the biomechanical model using pre-operative imaging data and intra-operative imaging data, the first region of the tissue of the patient including a first portion of an outer layer of the tissue of the patient and a first portion of an inner layer of the tissue of the patient;
   identifying correspondences between a second portion of the outer layer of the tissue of the patient of a second region of the tissue in the pre-operative imaging data and the second portion of the outer layer of the tissue of the patient of the second region of the tissue in the intra-operative imaging data; and
   determining a deformation of a second portion of the inner layer of the tissue of the patient of the second region of the tissue in the pre-operative imaging data based on the identified correspondences by applying the biomechanical model with the personalized biomechanical parameters.

2. The method as recited in claim 1, wherein extracting personalized biomechanical parameters from a first region of tissue of a patient in an inverse problem of the biomechanical model using pre-operative imaging data and intra-operative imaging data comprises:
   determining an initial deformation in the first region of the tissue in the pre-operative imaging data by applying the biomechanical model with standard biomechanical parameters;
   comparing the initial deformation in the first region of the tissue in the pre-operative imaging data with the first region of the tissue in the intra-operative imaging data; and
   iteratively updating biomechanical parameters of the biomechanical model based on the comparing to extract the personalized biomechanical parameters.

3. The method as recited in claim 2, wherein the standard biomechanical parameters include biomechanical parameters determined based on a population of patients.

4. The method as recited in claim 1, wherein:
   the first region of the tissue is a region of higher imaging accuracy in the inner layer of the tissue in the intra-operative imaging data, and
   the second region of the tissue is a region of lower imaging accuracy in the inner layer of the tissue in the intra-operative imaging data.

5. The method as recited in claim 1, wherein:
   the outer layer of the tissue includes a cortical layer of a brain of the patient, and
   the inner layer of the tissue include a subcortical layer of the brain of the patient.

6. The method as recited in claim 1, wherein extracting personalized biomechanical parameters from a first region of tissue of a patient in an inverse problem of the biomechanical model using pre-operative imaging data and intra-operative imaging data comprises:
   extracting personalized tissue elasticity and Poisson ratio of the patient.

7. The method as recited in claim 1, further comprising:
   updating the personalized biomechanical parameters based on a model of tumor growth for the patient.

8. An apparatus for image registration, comprising:
means for extracting personalized biomechanical parameters from a first region of tissue of a patient in an inverse problem of the biomechanical model using pre-operative imaging data and intra-operative imaging data, the first region of the tissue of the patient including a first portion of an outer layer of the tissue of the patient and a first portion of an inner layer of the tissue of the patient;
means for identifying correspondences between a second portion of the outer layer of the tissue of the patient of a second region of the tissue in the pre-operative imaging data and the second portion of the outer layer of the tissue of the patient of the second region of the tissue in the intra-operative imaging data; and
means for determining a deformation of a second portion of the inner layer of the tissue of the patient of the second region of the tissue in the pre-operative imaging data based on the identified correspondences by applying the biomechanical model with the personalized biomechanical parameters.

9. The apparatus as recited in claim 8, wherein the means for extracting personalized biomechanical parameters from a first region of tissue of a patient in an inverse problem of the biomechanical model using pre-operative imaging data and intra-operative imaging data comprises:
means for determining an initial deformation in the first region of the tissue in the pre-operative imaging data by applying the biomechanical model with standard biomechanical parameters;
means for comparing the initial deformation in the first region of the tissue in the pre-operative imaging data with the first region of the tissue in the intra-operative imaging data; and
means for iteratively updating biomechanical parameters of the biomechanical model based on the comparing to extract the personalized biomechanical parameters.

10. The apparatus as recited in claim 9, wherein the standard biomechanical parameters include biomechanical parameters determined based on a population of patients.

11. The apparatus as recited in claim 9, wherein the means for extracting personalized biomechanical parameters from a first region of tissue of a patient in an inverse problem of the biomechanical model using pre-operative imaging data and intra-operative imaging data comprises:
means for extracting personalized tissue elasticity and Poisson ratio of the patient.

12. The apparatus as recited in claim 9, further comprising:
means for updating the personalized biomechanical parameters based on a model of tumor growth for the patient.

13. A non-transitory computer readable medium storing computer program instructions for image registration, the computer program instructions when executed by a processor cause the processor to perform operations comprising:
extracting personalized biomechanical parameters from a first region of tissue of a patient in an inverse problem of the biomechanical model using pre-operative imaging data and intra-operative imaging data, the first region of the tissue of the patient including a first portion of an outer layer of the tissue and a first portion of an inner layer of the tissue;
identifying correspondences between a second portion of the outer layer of the tissue of a second region of the tissue in the pre-operative imaging data and the intra-operative imaging data; and
determining a deformation of a second portion of the inner layer of the tissue of the second region of the tissue in the pre-operative imaging data based on the identified correspondences by applying the biomechanical model with the personalized biomechanical parameters.

14. The non-transitory computer readable medium as recited in claim 13, wherein extracting personalized biomechanical parameters from a first region of tissue of a patient in an inverse problem of the biomechanical model using pre-operative imaging data and intra-operative imaging data comprises:
determining an initial deformation in the first region of the tissue in the pre-operative imaging data by applying the biomechanical model with standard biomechanical parameters;
comparing the initial deformation in the first region of the tissue in the pre-operative imaging data with the first region of the tissue in the intra-operative imaging data; and
iteratively updating biomechanical parameters of the biomechanical model based on the comparing to extract the personalized biomechanical parameters.

15. The non-transitory computer readable medium as recited in claim 13, wherein:
the first region of the tissue is a region of higher imaging accuracy in the inner layer of the tissue in the intra-operative imaging data, and
the second region of the tissue is a region of lower imaging accuracy in the inner layer of the tissue in the intra-operative imaging data.

16. The non-transitory computer readable medium as recited in claim 13, wherein:
the outer layer of the tissue includes a cortical layer of a brain of the patient, and
the inner layer of the tissue include a subcortical layer of the brain of the patient.

17. A method for image registration, comprising:
extracting personalized biomechanical parameters from a first region of tissue of a patient in an inverse problem of the biomechanical model using pre-operative imaging data and intra-operative imaging data;
identifying correspondences between an outer layer of a second region of the tissue in the pre-operative imaging data and the outer layer of the second region of the tissue in the intra-operative imaging data; and
determining a deformation of an inner layer of the second region of the tissue in the pre-operative imaging data based on the identified correspondences by applying the biomechanical model with the personalized biomechanical parameters;
wherein the first region of the tissue is a region of higher imaging accuracy in an inner layer of the tissue in the intra-operative imaging data, and
wherein the second region of the tissue is a region of lower imaging accuracy in the inner layer of the tissue in the intra-operative imaging data.

* * * * *